Figure 1:
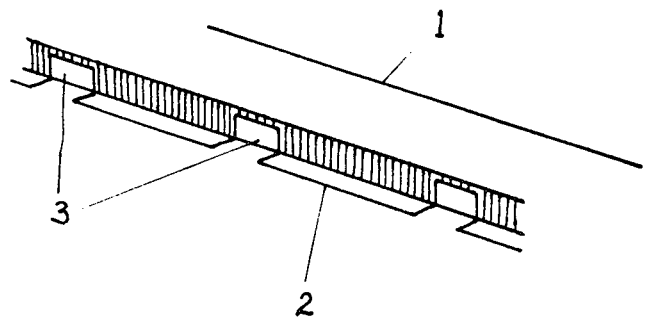

United States Patent [19]

Heden

[11] 4,076,591
[45] Feb. 28, 1978

[54] METHOD IN MICROBIOLOGICAL ANALYSIS

[76] Inventor: Carl-Goran Heden, Solna Kyrkvag 11, Solna, Sweden

[21] Appl. No.: 648,024

[22] Filed: Jan. 12, 1976

[30] Foreign Application Priority Data

Jan. 15, 1975 Sweden .............................. 75003905
Oct. 7, 1975 Sweden .............................. 75111963

[51] Int. Cl.² .............................................. C12K 1/04
[52] U.S. Cl. ..................... 195/103.5 K; 195/103.5 M; 195/127
[58] Field of Search ... 195/103.5 R, 103.5 K, 103.5 M

[56] References Cited

U.S. PATENT DOCUMENTS

| | | | |
|---|---|---|---|
| 2,771,398 | 11/1956 | Snyder | 195/103.5 R |
| 3,359,180 | 12/1967 | Evans et al. | 195/103.5 R |
| 3,416,998 | 12/1968 | Streitfeld | 195/103.5 R |
| 3,551,295 | 12/1970 | Dyer | 195/103.5 R |
| 3,632,478 | 1/1972 | Fink | 195/103.5 R |
| 3,715,280 | 2/1973 | Parmer | 195/103.5 R |
| 3,728,228 | 4/1973 | Duranty | 195/103.5 R |
| 3,826,717 | 7/1974 | Gilbert et al. | 195/103.5 R |

Primary Examiner—Alvin E. Tanenholtz
Assistant Examiner—Robert J. Warden
Attorney, Agent, or Firm—George H. Mitchell, Jr.

[57] ABSTRACT

In microbiological analysis wherein microorganisms are grown on an elongated substrate, a method which makes it possible to simultaneously study the effect of a number of different nutrition components on the growth of the organisms consists of dividing the elongated substrate into independent segments by inserting a series of transverse barriers therein to isolate each segment and to provide each segment with a reagent.

6 Claims, 6 Drawing Figures

METHOD IN MICROBIOLOGICAL ANALYSIS

The present invention refers to a method in microbiological analysis where a strain of microorganisms is made to grow on a substantially rectangular substrate-plate comprising a number of substrate components in order to make possible a simultaneous study of the effect of a number of different nutrition components on the growth of the organisms.

In the Swedish Pat. No. 344,368 and the Swedish patent application No. 7264/71, corresponding to U.S. Pat. No. 3,853,711, there is shown an equipment for automation of microbiological analysis. In this equipment the traditional petri-dishes for culturing microorganisms are replaced by rectangular substrate plates which are made from a big block of agar by means of cutting the block with a mechanically driven knife. These rectangular substrate plates, located on a suitable carrier such as a glass or plastic disk, constitute the culture medium and go through different automated steps such as adding sample, introduction into protection covers, incubation and evaluation of the microbiological reaction obtained. Usually a microorganism strain is inoculated across the surface or is inherent in the substrate. The substrate usually comprises a number of substrate components of a standard type for microbiological culturing or comprises a special mixture of substrate components. The substrate could for instance lack a number of important nutrition components which after the inoculation are added as reagents. The term reagent thus covers growth stimulating as well as growth inhibiting substances.

Typical areas of use for this automated microbiological analysis in numerical taxonomy, epidemiological "finger-printing", typing of gonococks and antibiotical resistance determinations. One usually starts out from a block of agar having a suitable composition for the strain of microorganisms used. From the agar block a substrate plate is cut along one edge of the agar block and the microorganism is spread over the surface of the substrate plate. Alternatively the agar block could be moulded in two or several segments of different composition. The cut bandshaped substrate will then consist of different parts comprising different types of agar substrate. In the type of analysis defined above one wants to test the effect of a number of reagents. The term reagent is then implying nutrition components which have been eliminated from the substrate of the agar block, e.g. specifically growth stimulating substances as well as specifically inhibiting substances. With this technique one thus wants to test a big number of reagents on one and the same microorganism. The different microbiological reactions which are obtained with the different reagents will thus give rise to a "finger-print" to be used for instance for taxonomical or epidemiological evaluation.

In order to use as little substrate as possible it is suitable in the procedure described above to add as many reagents as possible along the substrate plate consisting of the band cut from the agar block. The limiting factor is thereby the diffusion of the different reagents in the agar medium.

It is an object of the present invention to obtain a method for preventing diffusion between different parts of the substrate plate to which different reagents are added. It is another object with the invention to provide a method for fast and simple adding of different reagents to the substrate plate.

According to the invention diffusion barriers between different segments of the substrate plate are formed. A simple method for providing such barriers on the substrate plate consists in making grooves through the plate and to take away the material from the grooves. This could be made with a suitable punch for instance provided with a vacuum exhauster. Another method of obtaining these barriers consists in moulding diffusion barriers of polymer material at certain interval of the plate.

According to a preferred embodiment of the present invention a number of troughs are introduced into the substrate plate from one side. Each such trough consists of a bottom and two opposite sidewalls but is open at least in the direction of introduction. The mentioned opposite sides are suitably somewhat longer than the width of the substrate plate. According to a preferred embodiment of the present invention the specific reagent is adsorbed on the inside of the trough for instance at its bottom. When the trough is introduced into the gel a segment limited by diffusion barriers is obtained in the substrate plate and thereby the reagent is brought in contact with the substrate plate. In accordance with another embodiment of the invention the reagent consisting of non-diffusable particles (cells, fatty drops, starch granulate, etc.) are moulded into a gel with a low melting point, for instance a block of gelatine hanging on the edges of the trough. At the incubation temperature the block melts whereby the reagent is brought into contact with the substrate plate.

The characteristics of the invention appear from the claims attached to the specification.

Figure 2A:
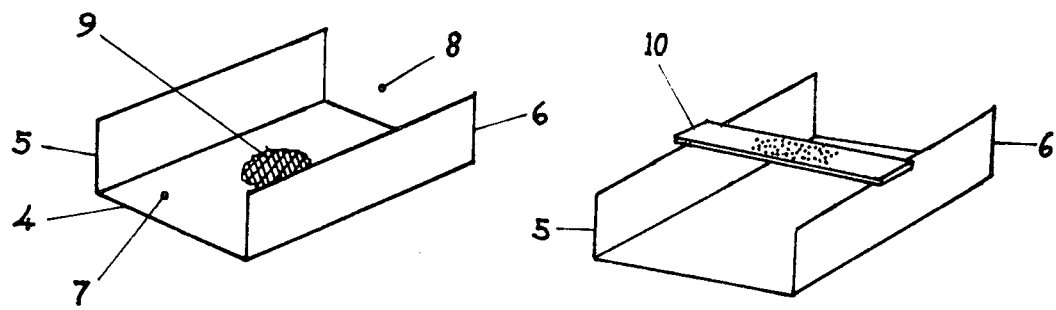
Figure 3:
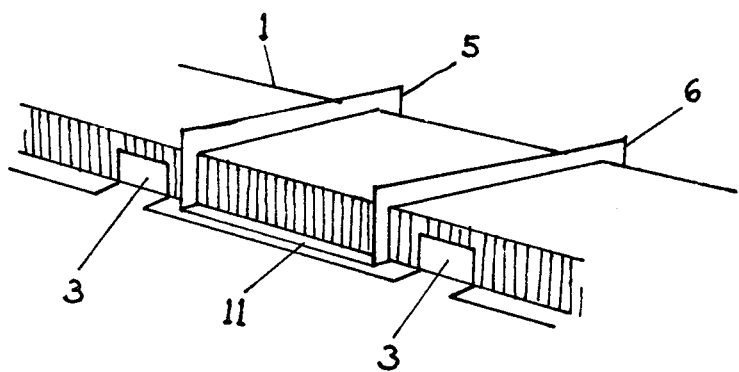
Figure 4:
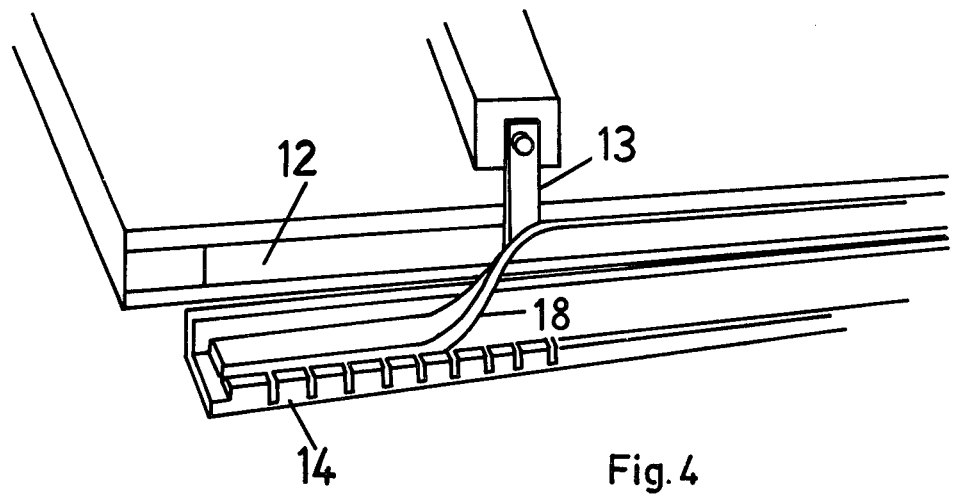
Figure 5:
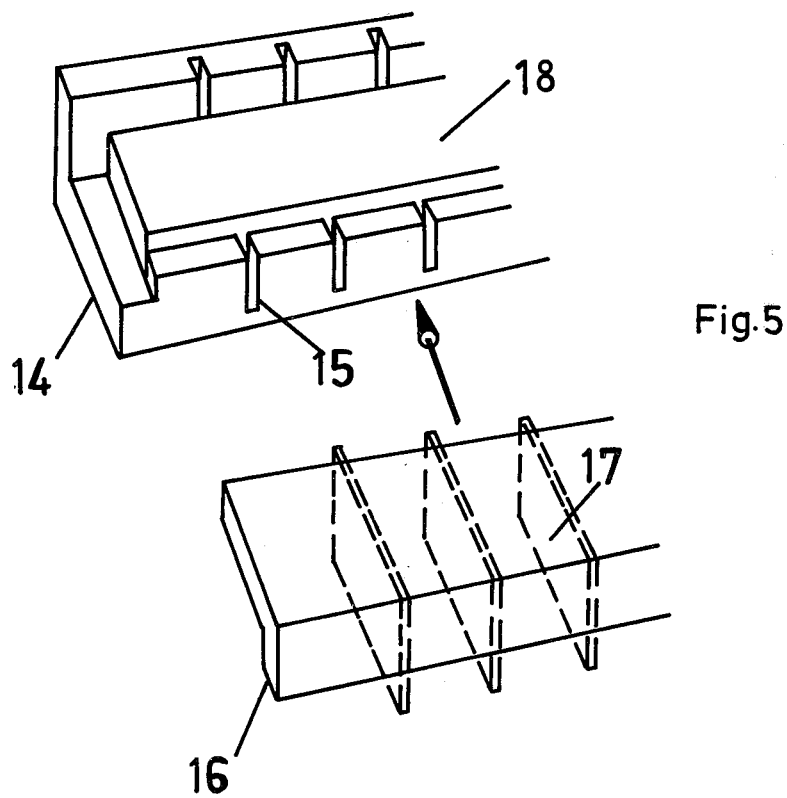

The invention will now be described in detail reference being made to the enclosed drawing in which:

FIG. 1 shows part of a substrate plate;

FIGS. 2a and b show troughs for use in a first embodiment of the method according to the invention FIG. 3 shows a trough introduced into the substrate plate FIGS. 4 and 5 show a second device for carrying out the method according to the invention.

In FIG. 1 reference 1 denotes a substrate plate. This plate rests on a carrier 2, consisting for instance of a plastic disk which is fed from a roller. At definite interval the edge of the carrier is folded to flanges 3.

In FIG. 2a reference 4 denotes the bottom of a trough with opposite sides 5 and 6. The ends 7 and 8 of the trough are open. Reference 9 denotes adsorbed reagent. In FIG. 2b reference 10 denotes a plate made from a gel, for instance gelatine, with an inherent reagent which is resting on the edges of the side walls 5 and 6 of the trough.

In FIG. 3 is shown a trough 11 introduced from one side into the inoculated substrate plate 1. The side walls 5 and 6 of the trough are wider than the width of the gel and are protruding at the opposite sides of the gel and also above the gel.

The embodiment shown works in the following way. The reagent desired is added to the trough for instance on its bottom by means of evaporation or some similar method. The opposite sides 5 and 6 of the trough shall suitably be longer than the width of the substrate plate and higher than the thickness of the plate. At least one of the sides 7 and 8 of the trough should be completely open and the trough is introduced in this direction into the inoculated substrate plate, preferably perpendicular to its length. Hereby mechanical shearing strain is generated in the substrate plate this strain being absorbed by the flanges 3. Suitably the flanges are arranged at such a distance from each other that a trough can be arranged between the flanges, since the bottom and sidewalls of the trough should protrude from the gel so as to constitute an efficient diffusion barrier. The reagent which is adsorbed at the bottom of the trough is at the introduction brought into contact with the substrate plate and the microbiological reaction is initiated. Along the elongated substrate plate such troughs are introduced as close to one another as permitted by the flanges 3, each trough being provided with a specific reagent or specific compound of reagents. After incubation one will then between the flanges have reference areas which makes it possible to carry out a simple optical quantification and data treatment of the reaction of the complete pattern found. An alternative way for adding the reagent is shown in FIG. 2b. The reagent is moulded into a plate of for instance gelatine which is resting on the top edges of the trough. After the trough has been introduced in the substrate plate the plate can be subject to incubation whereby the gel plate 10 should be made from a material that melts at the temperature of incubation. The reagent is then brought into contact with the top surface of the substrate plate 1 and the reaction is initiated.

Suitably a great number of troughs are introduced simultaneously from one side into a substrate plate preferably automatically by means of an introduction ruler or a similar instrument. The troughs are suitably introduced substantially perpendicular to the substrate plate but the angle of introduction could of course be varied. In order to make it possible to make the procedure automatic the troughs are suitably kept stored in stores from where they are easily accessible. The troughs should thereby be designed in a suitable way and could be provided with a top. This top could suitably be provided with an opening across which a gelatine plate 10 according to FIG. 2b could be put in case of adding a reagent to the top of the substrate plate.

Another embodiment of a device for carrying out the method according to the invention will now be described, reference being made to FIGS. 4 and 5.

In FIG. 4 reference 18 denotes a substrate plate which by means of a knife 13 is cut from a substrate block 12. At cutting the plate is placed on a support 14 which is provided with grooves 15 perpendicular to the longitudinal direction of the substrate plate. This is shown also in FIG. 5 and it should be observed that the grooves 15 also run along the bottom of the support 14. When the substrate plate is placed on the support 14 a number of partitions 17 acting as diffusion barriers are introduced, said partitions being fixed in a holder 16 at the same internal distance as the grooves 15. The partitions 17 thereby have a somewhat bigger surface than the cross sectional area of the substrate plate whereby they will slide into the grooves 15 and completely separate adjacent substrate plate segments from each other.

As in the embodiments described in the above mentioned patent application the different segments are suitably provided with a reagent before they are separated from each other. This can either be made by providing the different parts of the support 14 between the grooves 15 with a reagent or by arranging plates of gel, for instance gelatine, with an inherent reagent on the holder 16 between the partitions 17 whereby this plate is melted when the substrate plate is subjected to incubation whereby the reagent is added to the respective segments.

We claim:
1. Method of microbiological analysis wherein a simultaneous study is to be made of the effect of a number of different reagents on a strain of microorganisms comprising the steps of:
   a. forming an elongated plate of a substrate material which comprises a culture medium combined with a microorganism strain to analyzed;
   b. simultaneously inserting in a transverse direction into said elongated substrate plate a plurality of troughs, said troughs comprising a bottom and two opposite side walls but being open in the direction of said inserting, the bottom and side walls of the troughs constituting a plurality of completely isolated segments of substrate containing samples of said strain of microorganisms, and;
   c. introducing substantially simultaneously with said partitions a plurality of reagents for reaction with the microorganisms in the isolated segments of substrate.

2. Method according to claim 1, characterized in, that a reagent is molded into a gelatin plate which is suspended between the respective side walls of the troughs so that by melting of the gelatin plate at the culture temperature said reagent is brought into contact with said isolated segments of the substrate plate.

3. Method according to claim 1, characterized in, that said reagent is absorbed in the troughs prior to the introduction of the troughs into said substrate plate.

4. Method of microbiological analysis wherein a simultaneous study is to be made of the effect of a number of different reagents on a strain of microorganisms comprising the steps of:
   a. providing a narrow, elongated support;
   b. forming an elongated plate of a substrate material comprising a culture medium;
   c. depositing said substrate material on said support;
   d. inoculating a microorganism strain to be analyzed with said substrate along the length thereof;
   e. inserting transversely into said substrate plate a plurality of diffusion barrier partitions in a holder having reagent bearing meltable gel plates, each of said barriers having a width and height exceeding the cross-sectional dimensions of the substrate plate to form completely isolated segments of substrate containing samples of said strain of microorganisms and a reagent;
   f. introducing reagents on to said substrate for reaction with said microorganisms at a plurality of locations spaced along the length of said substrate at distances which are less than the distances to which said reagents are normally capable of diffusing in said substrate by incubating said holder so as to permit the gel plates to melt.

5. Method according to claim 4, characterized in, that the substrate plate is located on a support provided with grooves substantially perpendicular to the longitudinal direction of the substrate plate and said diffusion barriers are formed by walls having a width and a height exceeding the cross sectional dimensions of the substrate plate, whereby the partitions are simultaneously introduced into the substrate plate in alignment with said grooves and are inserted into the grooves.

6. Method according to claim 4, wherein said elongated support upon which the substrate material is deposited is provided with transverse grooves at said locations spaced along the length of the support to receive said diffusion barrier partitions.

* * * * *